United States Patent [19]
Cross et al.

[11] 3,933,470
[45] Jan. 20, 1976

[54] ESTER OF (ALKYNYLOXY)-, (ALKENYLOXY)-, AND (CYANOALKOXY) CARBANILIC ACIDS AND THEIR USE AS HERBICIDES

[75] Inventors: Barrington Cross, Rocky Hill; Robert Louis Arotin, Willingboro, both of N.J.

[73] Assignee: American Cyanamid Company, Stamford, Conn.

[22] Filed: May 24, 1974

[21] Appl. No.: 473,030

Related U.S. Application Data

[62] Division of Ser. No. 267,838, June 30, 1972, Pat. No. 3,852,532.

[52] U.S. Cl. ................... 71/111; 71/98; 71/101; 71/103
[51] Int. Cl.$^2$ ............................................ A01N 9/20
[58] Field of Search ............. 71/111, 101, 100, 103, 71/105

[56] References Cited
UNITED STATES PATENTS

| | | | |
|---|---|---|---|
| 2,992,091 | 7/1961 | Harman et al. | 71/101 |
| 3,406,192 | 10/1968 | Speziale et al. | 71/111 |
| 3,515,744 | 6/1970 | Steinbrunn et al. | 71/111 |
| 3,705,028 | 12/1972 | Janiak et al. | 71/120 |
| 3,781,327 | 12/1973 | Teach | 71/111 |
| 3,784,564 | 1/1974 | Rohr et al. | 71/111 |

*Primary Examiner*—Glennon H. Hollrah
*Attorney, Agent, or Firm*—H. G. Jackson

[57] ABSTRACT

The invention is novel esters of (alkynyloxy)-, (alkenyloxy)-, and (cyanoalkoxy) carbanilic acids and the thiono and dithio derivatives of the carbanilic acids, and their use for controlling broadleaf weeds and grasses.

9 Claims, No Drawings

ESTER OF (ALKYNYLOXY)-, (ALKENYLOXY)-, AND (CYANOALKOXY) CARBANILIC ACIDS AND THEIR USE AS HERBICIDES

This is a division, of application Serial No. 267,838, filed June 30, 1972 now U.S. Patent 3,852,532.

BACKGROUND OF THE INVENTION

1. Field of the Invention

The invention pertains to new chemical compounds and their use as herbicides.

2. Description of the Prior Art

The literature is replete with examples of herbicidal carbanilic acid esters as herbicides. One of the earliest is CIPC, the isopropyl ester of m-chlorocarbanilic acid which is a preemergence herbicide. Another is SWEP, the methyl ester of 3,4-dichlorocarbanilic acid, a selective preemergence herbicide in rice. Our invention describes carbanilates containing the hitherto undisclosed alkynyloxy, alkenyloxy and cyanoalkyloxy carbanilates. These compounds possess not only good preemergence activity but are equally effective postemergence, yet possess important crop selectivity. A general review of carbanilate esters is Weeds 2, pg 49, (1953). Further teachings are found in U.S. Pats. 2,695,225 (1954) and 3,116,995 (1964).

SUMMARY OF THE INVENTION

This invention is novel compounds of the formula:

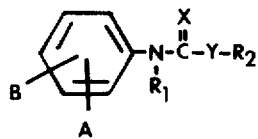

wherein A is hydrogen, halogen (Cl, Br, F, I), alkyl ($C_1$ -$C_4$), alkoxy ($C_1$ -$C_4$) monohaloalkyl ($C_1$ -$C_4$), dihaloalkyl ($C_1$ -$C_4$), trihaloalkyl ($C_1$ -$C_4$), nitro or $S(O)_nCH_3$ (n = 0, 1 or 2); B is

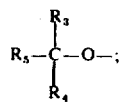

X and Y are oxygen or sulfur; $R_1$ is hydrogen or alkyl ($C_1$ -$C_4$); $R_2$ is straight or branched alkyl ($C_1$ -$C_{10}$) cycloalkyl ($C_3$ -$C_7$), benzyl, chlorobenzyl, methylbenzyl, phenyl, chlorophenyl, methylphenyl, alkenyl ($C_2$ -$C_6$), monohaloalkenyl ($C_2$ -$C_6$), alkynyl ($C_2$ -$C_6$), monohaloalkynyl ($C_2$ -$C_6$), monomethoxyalkynyl ($C_2$-$C_6$); $R_3$ and $R_4$ are hydrogen or methyl; $R_5$ is —CN,

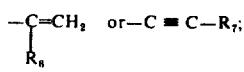

$R_6$ is hydrogen, methyl or halogen, and $R_7$ is hydrogen, alkyl ($C_1$ -$C_4$), alkoxyalkyl ($C_2$ -$C_6$), haloalkyl ($C_1$ -$C_4$), or halogen; provided that the members represented by A and B are respectively attached to the carbons in the ring which are meta- and para- to the carbon attached to the nitrogen, or they are respectively para- and meta- to the ring carbon attached to the nitrogen, and further provided that when B is $CH_2$ =$CH_2$ O-, X is oxygen. The compounds of the invention are useful for controlling a wide variety of broadleaf weeds and grasses. This utility involves the application of a herbicidally effective amount of a compound of the above formula to (1) the foliage or other plant parts of undesirable plant species, or (2) to soil containing seeds of undesirable plant species.

DESCRIPTION OF THE PREFERRED EMBODIMENTS

The invention is novel esters of (alkynyloxy)—, (alkenyloxy)—, and (cyanoalkoxy) carbanilic acids and their use for controlling undesirable vegetation. These esters can be prepared by several procedures.

To a m- or p-hydroxycarbanilate ester (II below) in a solvent such as acetone, alcohol (e.g. ethanol or methanol), DMF, etc., is added a molar equivalent of a base such as anhydrous sodium carbonate, potassium carbonate, potassium hydroxide, sodium hydroxide, sodium alkoxide (e.g. methoxide), potassium t-butoxide, butyl lithium or triethylamine. To the stirred mixture the alkynyl halide (1 to 2 moles) is added dropwise with stirring. The reaction temperature range is from 0°C. to 100°C., but 56°C. to 65°C. is generally preferable. After reaction for several hours (1 to 60 hours), the mixture is poured onto ice-water containing sodium carbonate or sodium acetate. A solid usually separates and is filtered off and crystallized. In some instances, it may be necessary to chloroform extract the solution and evaporate to a residual oil, followed by crystallization. The reaction may be graphically illustrated as follows:

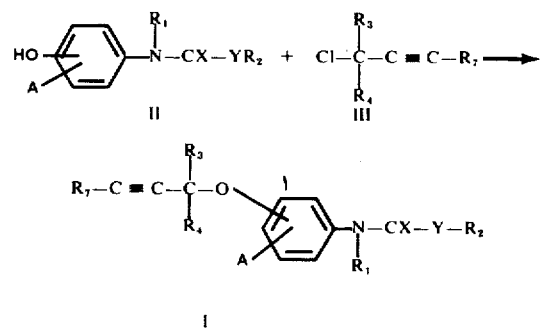

where $R_1$, $R_2$, $R_3$, $R_4$, $R_7$ and A are as defined above. This reaction is also useful for the preparation of the alkenyloxy- and cyanoalkoxycarbanilic acid esters (substituting allylic chlorides

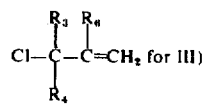

or substituting chloroacetonitriles

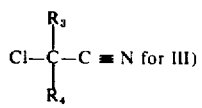

and the thiono and dithio derivatives thereof.

Alternatively, the (alkynyloxy)aniline (IV) is either reacted directly with a chloroformate ester (V) in an aprotic solvent (e.g. CH$_3$CN, DMF, acetone, THF) containing a base acceptor (either sodium bicarbonate or sodium carbonate as suspensions or triethylamine or pyridine). After reaction, usually at room temperature, the reaction mixture is poured onto ice-water containing 1N hydrochloric acid. The product separates out and is filtered off, dried and crystallized.

Treatment of a solution of (alkynyloxy)aniline (IV) in an aprotic solvent (ethyl acetate preferred) with an excess of phosgene, usually at reflux temperature affords the isocyanate (VI). Addition to the appropriate alcohol (R$_2$OH), usually at 50°C. to 60°C., affords the carbamate (I).

The compounds of the invention are readily soluble in many common organic solvents such as alcohols (e.g. methanol, ethanol, and isopropanol), ketones (e.g. acetone, methylethylketone, and cyclohexanone), and aromatic hydrocarbons (e.g. benzene, toluene, and xylene). This solubility characteristic is a significant advantage in formulating the compounds for use in the field since it permits preparation of a wide variety of liquid and solid formulations by relatively simple techniques. Emulsifiable concentrates can be prepared by dissolving from about 10% to 85% by weight of the active compound in an organic solvent or mixture of organic solvents (e.g. those mentioned above), and admixing with the thus-formed solution from about 1% to 10% by weight of an emulsifier or mixture of emulsi-

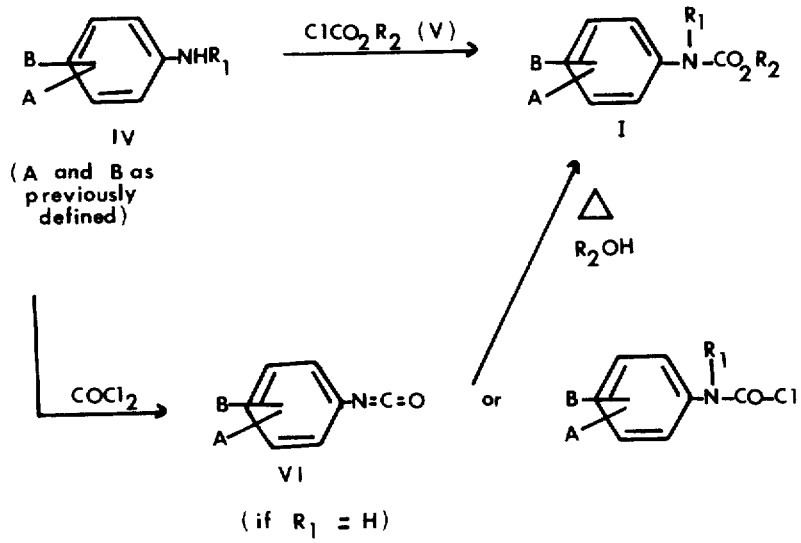

(A and B as previously defined)

(if R$_1$ = H)

In a similar manner, the intermediate m-or p-hydroxycarbanilate (II) ester is prepared from the appropriately substituted m- or p-aminophenol (VII) by either the agency of an alkyl chloroformate or preferably phosgene and an alcohol (R$_2$OH). The ease of the latter route is surprising since hydroxyphenylisocyanates are known to polymerize readily. However, the reaction with alcohols (R$_2$OH) is rapid, especially so with primary and secondary alcohols. (Table I below describes yields by procedures 1 or 2).

fiers. Among the emulsifiers which can be used are anionic-nonionic blends generally made up of oil soluble sulfonate calcium, or amine salts and polyoxyethylene ethers.

Wettable powders can be prepared by dissolving from about 10% to 85% by weight of the active compound in a lower alcohol (C$_1$ –C$_4$), ketone (C$_1$ –C$_6$), toluene, xylene, benzene, or the like, and spraying the thus-prepared solution on a finely ground inert diluent such as attapulgite, kaolin, diatomaceouos earth, talc,

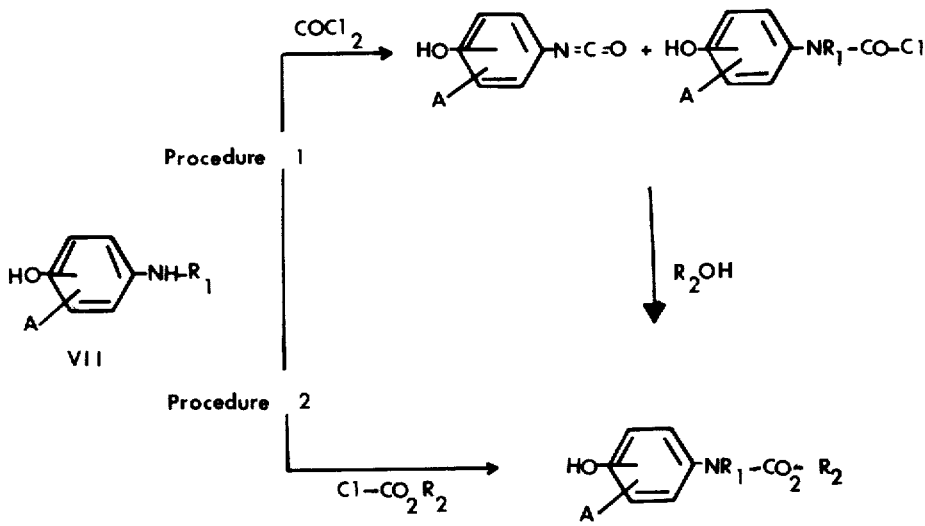

silica, pumice, or the like. Generally, about 1% to 10% by weight of a dispersing agent (e.g. sodium lignosulfonate or monocalcium salt of a polymerized alkylaryl sulfonic acid), and from 1% to 5% by weight of a wetting agent or surfactant (e.g. polyoxyethylated vegetable oil, alkylphenoxy polyoxyethylene ethanol, sodium alkylnaphthalene sulfonate, or ester of sodium isothionate), are also added to the formulation.

In practice, the wettable powder or emulsifiable concentrate is generally dispersed in water and applied as a liquid spray to the foliage of undesirable plants or to soil containing seeds of undesirable plants. The spray is generally applied in sufficient amount to provide about 0.2 pound to 15 pounds of active compound per acre of treated area. For selective control of broadleaf weeds and grasses in the presence of agronomic crops, usually only about 0.2 pound to 4 pounds of active compound per acre of treated area is required.

Where desired, the compounds of this invention may also be formulated as dusts, dust concentrates and granular formulations using conventional practices.

This invention is further illustrated by the examples set forth below.

EXAMPLES 1 AND 2

Preparation of m- and p-Hydroxycarbanilic Acid Esters 4-Hydroxycarbanilic Acid, Methyl Ester by Procedure 2

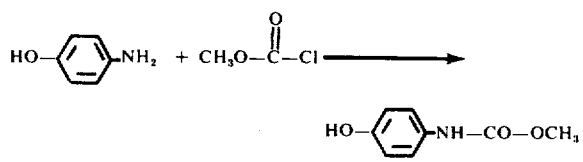

Methylchloroformate (48 grams, 0.5 mole) is added dropwise to a cooled (0°C. to 10°C.) stirred mixture of p-aminophenol (54.6 grams, 0.5 mole) and sodium bicarbonate (42 grams) in DMF (250 ml.). The mixture is allowed to attain 25°C. after 3 hours and a few drops of pyridine are added. After a further hour, the mixture is filtered and evaporated to a residual oil, which is stirred and scratched with 2N hydrochloric acid to give a solid. The solid is filtered off and crystallized from benzene to give 31.2 grams, 37%, melting point 113.5°C. to 114.5°C. or: Procedure 1

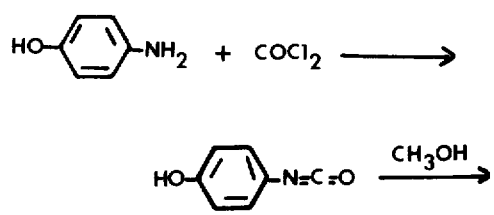

To a solution of phosgene (200 grams, 2 moles) in dry ethylacetate (1.5 liters) at 0°C. to 5°C. is added solid p-aminophenol (109.13 grams, 1 mole), and the mixture is stirred and heated at reflux for 1 ½ hours (phosgene being bubbled through for 30 minutes). The mixture becomes almost homogeneous and is cooled, filtered, and the filtrate concentrated to 800 ml. under reduced pressure. A 200 ml. portion of the isocyanate solution (0.25 mole) is added rapidly to methanol (1800 ml.). Then after one hour the mixture is warmed to reflux for 16 hours. The solvent is removed under reduced pressure, and the residue is crystallized from benzene to give the product, melting point 112°C. to 113.5°C., 26.7 grams, 65%.

EXAMPLE 3

Preparation of 3-Chloro-4-Hydroxycarbanilic Acid, Methyl Ester by Procedure 1

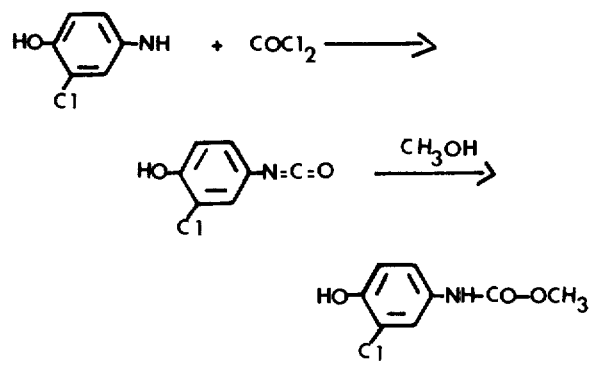

Powdered 4-amino-2-chlorophenol (210 grams, 1.46 moles) is added to a dry ethylacetate solution (2100 ml.) of phosgene (210 grams, 2.05 moles) and the mixture is stirred at 0°C. to 10°C. Slowly the reaction mixture is raised to reflux temperature after 1 hour. Further phosgene (20 grams) is passed through the solution during a one-half hour period, then the mixture is heated under reflux during another 30 minute period, cooled to 40°C., and rapidly filtered. The filtrate is evaporated under reduced pressure to a volume of 900 ml. An infrared spectrum of this oil has a peak at 2260 cm.$^{-1}$ (N=C=O). The isocyanate solution is added to methanol (1.8 liters) with stirring, and the reaction is brought to reflux for 16 hours, then set aside at 20°C. for 48 hours. Evaporation of the reaction mixture affords a viscous oil. Addition of benzene (2 × 300 ml.) followed by evaporation causes the oil to solidify. The crude solid is vacuum dried, melting point 96°C. to 98°C., 250.5 grams (86%). Crystallization of a 5 gram sample from benzene (trace n-hexane) affords crystals, melting point 104°C. to 105°C., 2.76 grams (47%).

EXAMPLES 4 THROUGH 9

(Procedure as Example 1)

Preparation of 3-Chloro-4-Hydroxycarbanilic Acid, Isopropyl Ester and Derivatives Thereof by Procedure 2

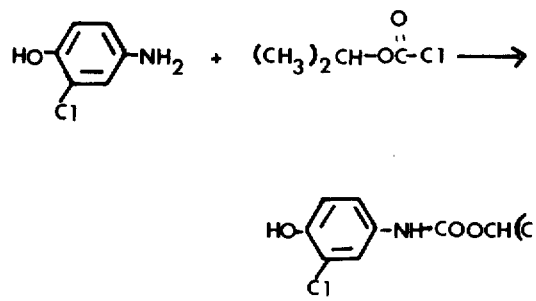

To a solution of 4-amino-2-chlorophenol (21.45 grams, 0.15 mole) in dry DMF (150 ml.) and pyridine (11.8 grams) is added at 0°C. slowly dropwise with stirring isopropyl chloroformate (16.5 grams, 0.016 mole). After 4 hours at 0° C. to 5°C., a further one gram of isopropyl chloroformate is added. The mixture is stirred at 25°C. for 16 hours, then poured into ice-dilute hydrochloric acid. After 4 hours stirring and scratching, a solid separates out and is filtered off. Crystallization from methanol gives 14.5 grams, 42%, melting point 89°C. to 90°C.

Following the procedure of Examples 1 or 2 above, but utilizing the appropriate phenol and chloroformate or appropriate alcohol and phosgene in the reaction, yields the compounds listed below in Table I.

TABLE I

| Example Number | Structure | Melting Point °C. | Solvent of Crystallization | % Yield | Procedure |
| --- | --- | --- | --- | --- | --- |
| 5 | HO-⟨⟩-NHCO$_2$CH(CH$_3$)$_2$ | 102–103 | toluene-cyclohexane | 32 | 1 |
| 6 | HO-⟨⟩-NH-CO$_2$-CHCH$_3$-C≡CH | 102.5–103.5 | benzene | 10 | 1 |
| 7 | HO-⟨⟩-NH-CO$_2$-C$_3$H$_7$-n (Cl) | | benzene-hexane | | 1 |
| 8 | ⟨⟩-NH-CO$_2$-CH$_3$ (OH) | 94.5–95.5 | benzene | 47 | 2 |
| 9 | HO-⟨⟩-NH-CO$_2$-⟨⟩ | 112–113 | benzene | 29 | 1 |
| 10 | HO-⟨⟩-NH-CO$_2$-C$_2$H$_5$ (Cl) | | benzene | | 1 |
| 11 | HO-⟨⟩-NH-CO$_2$-C$_2$H$_5$ | 119–120 | benzene | 62 | 1 |
| 12 | HO-⟨⟩-NH-CO$_2$CH$_2$-CH=CH$_2$ | 109–110 | benzene | 52 | 1 |
| 13 | HO-⟨⟩-NH-CO$_2$CH$_2$CH$_2$CH$_3$ | 97–98 | benzene | 63 | 1 |
| 14 | HO-⟨⟩-NH-CO$_2$CH$_2$-C≡CH | 114–117 | benzene | 45 | 1 |
| 15 | HO-⟨⟩-NH-CO$_2$-CH$_2$-⟨⟩ | 155–156 | benzene | 83 | 1 |
| 16 | HO-⟨⟩-NHCO$_2$C(CH$_3$)$_3$ | 142–143 | benzene | 31 | 1 |
| 17 | HO-⟨⟩-NHCO$_2$CH$_3$ (NO$_2$) | 139–140 | benzene | 52 | 1 |

TABLE I-continued

| Example Number | Structure | Melting Point °C. | Solvent of Crystallization | % Yield | Procedure |
|---|---|---|---|---|---|
| 18 | HO–⟨⟩–NH–CO₂CH₃ with OCH₃ | | | | |
| 19 | HO–⟨⟩–NHCO₂CH₃ with CH₃ | | | | |
| 20 | HO–⟨⟩–NHCO₂CH₃ with Br | | | | |

EXAMPLE 21

Preparation of 3-Chloro-4-(2-Propynyloxy)Carbanilic Acid, Isopropyl Ester

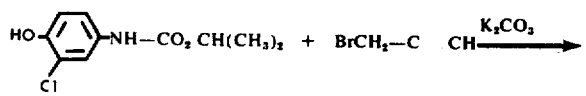

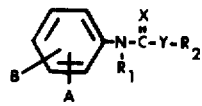

Propargyl bromide (1.79 grams, 0.015 mole) is added dropwise to a stirred mixture of the isopropyl ester of 3-chloro-4-(hydroxy)carbinilic acid (3.45 grams, 0.015 mole), and anhydrous potassium carbonate (2.08 grams, 0.015 mole) in dry acetone (50 ml.). The mixture is stirred at reflux during 18 hours, then poured into 2% aqueous sodium carbonate (400 ml.). After stirring for 1 hour, a beige solid separates and is filtered off and air dried. Crystallization from cyclohexane affords long needles, 3.45 grams, 86%, melting point 79°C. to 79.5°C.

EXAMPLE 22

Following the procedure of Example 21 and substituting the appropriate carbanilic acid ester for the isopropyl ester of 3-chloro-4-(hydroxy)carbanilic acid and the appropriate alkenyl halide, alkynyl halide or cyanoalkyl halide for propargyl bromide, yields the compounds idenfified below in Table II.

TABLE II

Compounds Having the Structure: (aryl with B, A substituents)–N(R₁)–C(=X)–Y–R₂    Prepared by the Procedure Above

| B | A | R₁ | X | Y | R₂ | Solvent of Crystallization | Melting Point °C. |
|---|---|---|---|---|---|---|---|
| 4–HC≡C–CH(CH₃)–O– | 3–Cl | H | O | O | CH₃ | | |
| 4–HC≡C–C(CH₃)₂–O– | 3–Cl | H | O | O | CH₃ | | |
| 4–HC≡C–CH₂–O– | H | H | O | O | CH₃ | cyclohexane | 75–75.3 |
| 4–I–C≡C–CH₂–O– | H | H | O | O | CH₃ | | |
| 4–Cl–CH₂–C≡C–CH₂–O– | H | H | O | O | CH₃ | | |
| 4–CH₃–O–CH₂–C≡C–CH₂–O– | H | H | O | O | CH₃ | | |
| 3–HC≡C–CH₂–O– | H | H | O | O | CH₃ | hexane-cyclohexane | 49.5–50 |
| 4–HC≡C–CH₂–O– | 3–Cl | H | O | S | CH₃ | | |
| 4–HC≡C–CH₂–O– | 3–Cl | H | S | S | CH₃ | | |
| 4–HC≡C–CH₂–O– | H | H | O | O | –⟨⟩–Cl | | |

TABLE II-continued

Compounds Having the Structure: 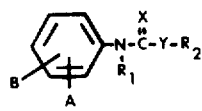 Prepared by the Procedure Above

| B | A | R₁ | X | Y | R₂ | Solvent of Crystallization | Melting Point °C. |
|---|---|---|---|---|---|---|---|
| 4—HC≡C—CH₂—O— | H | H | O | O | —CH₂—C₆H₅ | cyclohexane | 86–87 |
| 4—HC≡C—CH₂—O— | 3—Br | H | O | O | CH₃ | | |
| 4—HC≡C—CH₂—O— | 3—CF₃ | H | O | O | CH₃ | | |
| 4—HC≡C—CH₂—O— | 3—CH₃ | H | O | O | CH₃ | | |
| 4—HC≡C—CH₂—O— | 3—OCH₃ | H | O | O | CH₃ | | |
| 4—HC≡C—CH₂—O— | 3—CN | H | O | O | CH₃ | | |
| 4—HC≡C—CH₂—O— | 3—SCH₃ | H | O | O | CH₃ | | |
| 4—HC≡C—CH₂—O— | 3—NO₂ | H | O | O | CH₃ | | |
| 4—CH≡C—CH₂—O— | 3—Br | H | O | O | CH₃ | | |
| 4—HC≡C—CH₂—O— | H | H | O | O | —C(CH₃)₂—C≡CH | | |
| 4—HC≡C—CH₂—O— | H | H | O | O | —CH₂—CH=CH₂ | hexane | 42–43 |
| 3—HC≡C—CH₂—O— | 4—Cl | H | O | O | CH₃ | | |
| 4—HC≡C—CH₂—O— | 3—Cl | H | O | O | —C₂H₅ | | |
| 4—HC≡C—CH₂—O— | 3—Cl | H | O | O | —C₃H₇—n | | |
| 4—HC≡C—CH₂—O— | 3—Cl | H | O | O | —C(CH₃)₃ | | |
| 4—HC≡C—CH₂—O— | 3—Cl | H | O | O | —CH(CH₃)—C≡CH | | |
| 4—HC≡C—CH₂—O— | 3—Cl | H | O | O | —CH₂—C≡CH | | |
| 4—HC≡C—CH₂—O— | 3—Cl | H | O | O | —CH₂—C≡C—CH₂Cl | | |
| 4—HC≡C—CH₂—O— | 3—Cl | H | S | O | —C₆H₁₁ | | |
| 4—HC≡C—CH₂—O— | 3—Cl | H | O | O | —C₆H₁₁ | | |
| 4—HC≡C—CH₂—O— | 3—Cl | H | O | O | —C₆H₅ | | |
| 4—CH₂=CH—CH₂—O— | 3—H | H | O | O | CH₃ | hexane | 73–73.5 |
| 3—CH₂=CH—CH₂—O— | 4—H | H | O | O | CH₃ | cyclohexane | 10–15 |
| 4—HC≡C—CH₂—O— | 3—H | H | O | O | —C₂H₅ | cyclohexane | 50–50.5 |
| 4—HC≡C—CH₂—O— | 3—H | H | O | O | —CH(CH₃)₂ | hexane | 72.5–73 |
| 4—CN—CH(CH₃)—O— | 3—CH₂Cl | —CH₃ | S | O | —C₂H₅ | hexane | |
| 4—CH₂=C(CH₃)—CH₂—O— | 3—CH₂—CH(Cl)—CH₂Cl | H | O | O | —CH₃ | hexane | |
| 4—CH₃—C≡C—CH₂—O— | 3—CF₃ | H | S | S | —C₃H₇—n | | |
| 3—C₃H₇—C≡C—CH₂—O— | 4—NO₂ | —C₃H₇ | O | S | C₆H₁₁ | | |
| 4—CH≡C—CH(CH₃)—O— | 3—SO₂CH₃ | H | S | S | —CH₃ | hexane- | |

TABLE II-continued

Compounds Having the Structure:    Prepared by the Procedure Above

| B | A | $R_1$ | X | Y | $R_2$ | Solvent of Crystallization | Melting Point °C. |
|---|---|---|---|---|---|---|---|
| 4—HC≡C—CH$_2$—O— | 3—Cl | —CH$_3$ | O | O | 4—Cl—C$_6$H$_4$—CH$_2$— | cyclohexane | |
| 4—HC≡C—CH$_2$—O— | H | —C$_2$H$_5$ | S | O | 4—CH$_3$—C$_6$H$_4$—CH$_2$— | | |
| 4—HC≡C—CH$_2$—O— | 3—SCH$_3$ | H | O | S | 4—Cl—C$_6$H$_4$ | | |
| 4—Br—C≡C—CH$_2$—O— | 3—C$_3$H$_5$Br$_2$ | H | S | S | 4—CH$_3$—C$_6$H$_4$— | | |
| 4—HC≡C—CH—O—<br>    \|<br>    CH$_3$ | 3—NO$_2$ | CH$_3$ | O | S | ClCH$_2$CH=CH—CH$_2$— | | |
| 4—Br—CH$_2$—C≡C—CH$_2$—O— | 3—Br | H | S | S | CH$_3$OCH$_2$—C≡C—CH$_2$— | | |
| 4—CH≡C—CH$_2$—O— | 3—H | H | O | O | —CH$_2$—C≡CH | cyclohexane | 69–71 |
| 4—CH≡C—CH$_2$—O— | 3—H | H | O | O | —CH—C≡CH<br>  \|<br>  CH$_3$ | n-hexane | 65–66 |
| 4—CH≡C—CH$_2$—O— | 3—H | H | O | O | —C$_3$H$_7$—n | n-hexane | 42–42.5 |
| 4—CH≡C—CH$_2$—O— | 3—H | H | O | O | C$_6$H$_{11}$ | n-hexane | 73–74.5 |
| 4—CH≡C—CH$_2$—O— | 3—H | H | O | O | C(CH$_3$)$_3$ | cyclohexane | 79–80 |
| 4—CH$_2$=C—CH$_2$—O—<br>      \|<br>      Cl | 3—Cl | H | O | O | CH$_3$ | | |

EXAMPLE 23

Preparation of 3-Chloro-4-(2-propynyloxy)carbanilic Acid, Methyl Ester

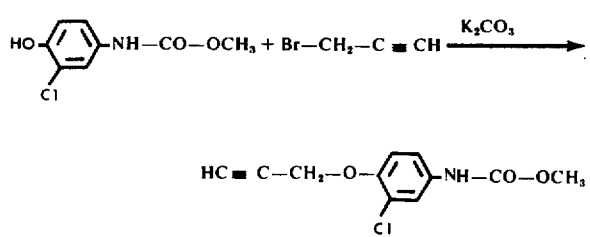

Propargyl bromide (130 grams, 1.1 moles) is added to a mixture of the methyl ester of 3-chloro-4-hydroxycarbanilic acid (213 grams, 1.06 moles) and anhydrous potassium carbonate (152 grams, 1.1 moles) in dry acetone (2.5 liters), and the mixture stirred and heated under reflux during 21 hours, cooled and poured into ice water containing 5% sodium carbonate. A solid separates out and is filtered off and air dried to give 250 grams, 99%, melting point 124°C. to 124.5°C. Crystallization from benzene/hexane gives pure product, melting point 126°C. to 126.5°C., 173 grams (69%). Infrared and nuclear magnetic resonance are superimposable with the product prepared by other procedures.

EXAMPLE 24

Preparation of 3-Chloro-4-(2-propynyloxy)carbanilic Acid, Methyl Ester

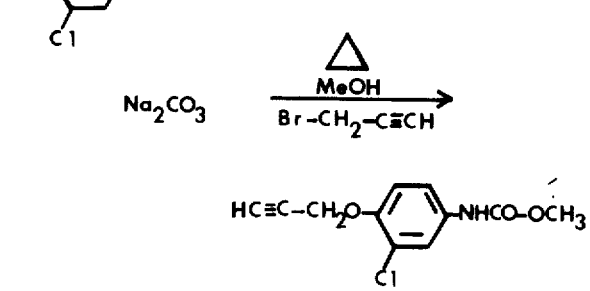

One mole of 3-(3-chloro-4-hydroxyphenyl)-1,1-dimethylurea is dissolved in 2510 ml. of absolute methanol, and then 1.5 moles of sodium carbonate is added and the mixture refluxed for one hour. A solution of 500 ml. of methanol containing 1.0 mole of propargyl bromide is then added, over an extended period, to the reaction mixture at a rate sufficient to maintain the temperature at reflux. After the addition is complete, the mixture is refluxed for an additional 9 ½ hours.

The reaction is then cooled and poured into ice and water containing 1% of sodium carbonate. After about 15 minutes, a precipitate forms. However, the mixture is stirred for an additional hour, then filtered, washed, and dried.

The crude material from above is passed through a dry silica gel column eluting with benzene. The product is located on the column, cut out and extracted with methanol. The methanol is then removed leaving an off-white solid, melting pont 120°C. to 122°C., which is crystallized using benzene/hexane to white crystals having a melting point of 122.5°C. to 123.5°C. It is not certain if the methoxide displacement of dimethylamine to give this product occurs directly on the ureidophenol or on the propargyloxyphenylurea or on both.

EXAMPLE 25

The selective postemergence herbicidal activity of the preferred compounds of the present invention is demonstrated by the following tests, wherein a variety of monocotyledonous and dicotyledonous plants are treated with test compounds dispersed in aqueous acetone mixtures. In the tests, seedling plants are grown in plastic pots for about two weeks. The test compounds are dispersed in 50/50 acetone/water mixtures containing 0.5% v/v surfactant in sufficient quantity to provide the equivalent of about 0.19 to 10 pounds per acre of active compound when applied to the plants through a spray nozzle operating at 40 psi. for a predetermined time. After spraying, the plants are placed on greenhouse benches and are cared for in the usual manner, commensurate with conventional greenhouse practices. Two weeks after treatment, the seedling plants are examined and rated according to the rating system provided below. The data obtained are reported in the Table below where it can be seen that the preferred compounds are highly effective for the control of undesirable broadleaf weeds and grasses.

The specificity of the compounds of the invention for control of weeds and grasses in the presence of rice is particularly well demonstrated by these tests.

| Rating System: | % Difference in Growth from the Check* |
|---|---|
| 0 — no effect | 0 |
| 1 — possible effect | 1–10 |
| 2 — slight effect | 11–25 |
| 3 — moderate effect | 26–40 |
| 5 — definite injury | 41–60 |
| 6 — herbicidal effect | 61–75 |
| 7 — good herbicidal effect | 76–90 |
| 8 — approaching complete kill | 91–99 |
| 9 — complete kill | 100 |
| 4 — abnormal growth, i.e. a definite physiological malformation but with an over-all effect less than a 5 on the rating scale. | |

*Based on visual determination of stand, size, vigor, chlorosis, growth malformation and over-all plant appearance.

Plant Abbreviations:

| | |
|---|---|
| LA — Lambsquarters | GRF — Green foxtail |
| MU — Mustard | WO — Wild oats |
| PI — Pigweed | COR — Corn |
| BA — Barnyard grass | COT — Cotton |
| CR — Crabgrass | SOY — Soybean |
| RAG — Ragweed | MG — Morning-glory |
| R — Rice | VE — Velvetleaf |
| TO — Tomato | |

TABLE III

Postemergence Herbicidal Activity

| Structure | Treatment lb./Acre | MU | PI | RAG | CR | GRF | WO | VE | COR | COT | SOY | R | TO |
|---|---|---|---|---|---|---|---|---|---|---|---|---|---|
| | | A | | | G | A | | | | | | | |
| 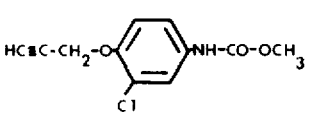 | 9 | 9 | 9 | 9 | 9 | 9 | 9 | 9 | 8 | 9 | 8 | 9 | 9 | 7 |
| | 3 | 9 | 9 | 9 | 9 | 9 | 8 | 9 | 7 | 9 | 7 | 9 | 9 | 5 |
| | 1.5 | 9 | 9 | 9 | 8 | 9 | 9 | 9 | 6 | 6 | 9 | 7 | 9 | 2 |
| | 0.75 | 9 | 9 | 9 | 9 | 7 | 9 | 9 | 9 | 3 | 3 | 6 | 6 | 7 | 2 |
| | 0.38 | 9 | 9 | 9 | 9 | 2 | 8 | 9 | 9 | 2 | 0 | 7 | 6 | 3 | 2 |
| | 0.19 | 9 | 8 | 9 | 9 | 1 | 7 | 8 | 7 | 1 | 0 | 1 | 3 | 3 | 1 |
| 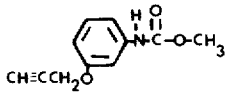 | 10 | 9 | 6 | 5 | 0 | 6 | 3 | 3 | 2 | 2 | 6 | | | 7 |
| 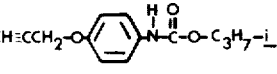 | 10 | 8 | 6 | 8 | 0 | 6 | 2 | 3 | 3 | 1 | 2 | | | 6 |
| 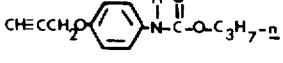 | 10 | 8 | 7 | 8 | 0 | 2 | 2 | 3 | 3 | 2 | 0 | | | 2 |
| 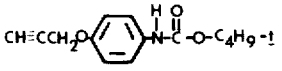 | 10 | 6 | 4 | 8 | 0 | 4 | 3 | 4 | 2 | 0 | 0 | | | 2 |
| 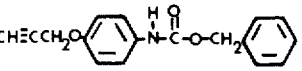 | 10 | 6 | 3 | 9 | 0 | 6 | 1 | 6 | 2 | 0 | 2 | | | 6 |

TABLE III-continued

Postemergence Herbicidal Activity

| Structure | Treatment lb./Acre | MU | | PI | RAG | | | CR | GRF | WO | VE | COR | COT | SOY | R | TO |
|---|---|---|---|---|---|---|---|---|---|---|---|---|---|---|---|---|
| | | | A | | | G | A | | | | | | | | | |
| CH≡CCH₂O-[Ar(Cl)]-N(H)C(O)-O-C₃H₇-i | 10 | 9 | 9 | 9 | 3 | 9 | 6 | 9 | 9 | 5 | 2 | | | | | 9 |
| | 2 | 9 | 9 | 9 | 8 | 9 | 2 | 9 | 9 | 2 | 1 | 1 | 5 | 3 | 1 | |
| CH₂=CHCH₂O-[Ar]-N(H)C(O)-O-CH₃ | 10 | — | 8 | 8 | 7 | 3 | 5 | 5 | 3 | 2 | 0 | | | | | 2 |
| | 2 | 8 | 9 | 9 | 2 | 8 | 0 | 2 | 8 | 1 | 2 | 1 | 9 | 3 | 0 | |
| [Ar(OCH₂C≡CH)]-N(H)C(O)-O-CH₃ | 10 | 9 | 5 | 9 | 3 | 3 | 6 | 8 | 8 | 3 | 2 | | | | | 5 |
| | 2 | 9 | 9 | 9 | 8 | 9 | 1 | 2 | 2 | 1 | 7 | 1 | 9 | 6 | 1 | |
| CH≡CCH₂O-[Ar]-N(H)C(O)-O-C₂H₅ | 10 | 9 | 6 | 8 | 3 | 3 | 3 | 2 | 2 | 0 | 3 | | | | | 6 |
| CH≡CCH₂O-[Ar]-N(H)C(O)-O-[cyclohexyl] | 10 | 3 | 3 | 6 | 0 | 4 | 0 | 4 | 4 | 0 | 0 | | | | | 1 |
| CH≡CCH₂O-[Ar]-N(H)C(O)-O-CH₂C≡CH | 10 | 9 | 4 | 6 | 0 | 4 | 2 | 6 | 2 | 0 | 0 | | | | | 8 |
| CH≡CCH₂O-[Ar]-N(H)C(O)-O-CH(CH₃)C≡CH | 10 | 5 | 3 | 3 | 0 | 3 | 0 | 6 | 2 | 0 | 0 | | | | | 3 |
| CH₂=CHCH₂O-[Ar(Cl)]-N(H)C(O)-O-CH₃ | 10 | 9 | 9 | 9 | 7 | 9 | 9 | 9 | 9 | 9 | 7 | | | | | 9 |
| | 2 | 9 | 9 | 9 | 9 | 9 | 6 | 7 | 9 | 3 | 7 | 2 | 9 | 7 | 1 | |
| | .25 | 9 | 8 | 8 | .3 | 7 | 0 | 0 | 0 | 0 | 0 | 1 | 2 | 2 | 0 | |
| | .13 | 9 | 1 | 3 | 0 | 1 | 0 | 0 | 0 | 0 | 0 | 0 | 1 | 1 | 0 | |
| | .06 | 5 | 0 | 2 | 0 | 0 | 0 | 0 | 0 | 0 | 0 | 0 | 0 | 0 | 0 | |
| | .03 | 0 | 0 | 0 | 0 | 0 | 0 | 0 | 0 | 0 | 0 | 0 | 0 | 0 | 0 | |

EXAMPLE 26

The selective preemergence herbicidal activity of the compounds of the invention is exemplified by the following tests in which the seeds of a variety of monocotyledonous and dicotyledonous plants are separately mixed with potting soil and planted on top of approximately one inch of soil in separate 2-inch plastic pots. After planting, the pots are sprayed with the selected aqueous acetone solution containing test compound in sufficient quantity to provide the equivalent of about 0.38 to 10 pounds per acre of test compound per pot. The treated pots are then placed on greenhouse benches and cared for in accordance with greenhouse procedures. Three weeks after treatment, the tests are terminated and each pot is examined and rated according to the rating system set forth in the preceding example. The tabulated results of these tests establish the selective herbicidal proficiency of the test compounds, when properly applied, for controlling a variety of undesirable plant species. The specificity of the compounds of the invention for weeds and grasses in the presence of rice, corn, cotton and soybeans, is particularly well demonstrated by these tests. Note that many broadleaf and grass weeds which are common to corn, cotton and rice culture are controlled by the compounds described in this invention with little or no damage to the desired crop plants. Data obtained are reported in the Table below.

TABLE IV

Preemergence Herbicidal Activity

| Structure | Treatment lb./Acre | MU | PI | RAG | | CR | GRF | WO | VE | COR | COT | SOY | R | TO |
|---|---|---|---|---|---|---|---|---|---|---|---|---|---|---|
| | | A | | | G A | | | | | | | | | |
| HC≡C–CH₂–O–C₆H₃(Cl)–NH–CO–OCH₃ | 9 | 9 | 9 | 9 | 9 9 | 9 | 9 | 9 | 7 | 3 | 1 | 2 | 2 | 7 |
| | 3 | 9 | 9 | 9 | 9 9 | 9 | 9 | 7 | 0 | 0 | 2 | 0 | 7 | 0 |
| | 1.5 | 9 | 8 | 9 | 9 1 | 8 | 9 | 9 | 0 | 0 | 0 | 0 | 7 | 0 |
| | 0.75 | 9 | 0 | 9 | 7 0 | 7 | 8 | 8 | 0 | 0 | 0 | 0 | – | 0 |
| | 0.38 | 8 | 0 | 7 | 3 0 | 3 | 3 | 2 | 0 | 0 | 0 | 0 | 0 | 0 |
| CH≡CCH₂O–C₆H₃(Cl)–NHC(O)–O–C₃H₇-i | 10 | 8 | 7 | 9 | 0 3 | 5 | 9 | 7 | 3 | 0 | | | | 7 |
| | 4 | 8 | 6 | 9 | 0 0 | 0 | 6 | 1 | 0 | 0 | 0 | 0 | 0 | 0 |
| CH₂=CHCH₂O–C₆H₄–NHC(O)–O–CH₃ | 10 | 6 | 9 | 9 | 3 9 | 7 | 8 | 8 | 0 | 0 | | | | 7 |
| | 4 | 5 | 8 | 8 | 2 3 | 3 | 5 | 5 | 0 | 0 | 0 | 2 | 0 | 1 |
| m-(CH≡CCH₂O)C₆H₄–NHC(O)–O–CH₃ | 10 | 8 | 9 | 8 | 6 7 | 6 | 3 | 2 | 0 | 2 | | | | 7 |
| | 4 | 6 | 8 | 5 | 2 5 | 3 | 3 | 2 | 2 | 0 | 0 | 0 | 2 | 3 |
| CH≡CCH₂O–C₆H₄–NHC(O)–O–C₂H₅ | 10 | 8 | 9 | 8 | 7 3 | 3 | 3 | 5 | 0 | 0 | | | | 3 |
| | 4 | 3 | 7 | 3 | 0 0 | 0 | 0 | 0 | 1 | 0 | 0 | 0 | 0 | 0 |
| m-(CH≡CCH₂O)C₆H₄–NHC(O)–O–CH₃ | 10 | 7 | 9 | 5 | 7 3 | 8 | 7 | 6 | 3 | 2 | | | | 5 |
| | 4 | 9 | 7 | 8 | 0 0 | 2 | 0 | 0 | 0 | 0 | 0 | 3 | 0 | 0 |
| CH≡CCH₂O–C₆H₄–NHC(O)–O–C₃H₇-i | 10 | 7 | 9 | 9 | 3 3 | 3 | 6 | 6 | 3 | 0 | | | | 2 |
| | 4 | 8 | 5 | 9 | 3 1 | 1 | 3 | 0 | 0 | 2 | 0 | 3 | 9 | 0 |
| CH≡CCH₂O–C₆H₄–NHC(O)–O–C₃H₇-n | 10 | 7 | 9 | 9 | 3 2 | 5 | 6 | 7 | 2 | 0 | | | | 0 |
| | 4 | 7 | 2 | 7 | 0 7 | 0 | 0 | 0 | 1 | 0 | 0 | 0 | 1 | 0 |
| CH≡CCH₂O–C₆H₄–NHC(O)–O–C₄H₉-t | 10 | 7 | 7 | 8 | 2 0 | 3 | 8 | 8 | 0 | 0 | | | | 1 |
| | 4 | 9 | 8 | 8 | 9 2 | 7 | 7 | 8 | 2 | 1 | 0 | 0 | 2 | 1 |
| CH≡CCH₂O–C₆H₄–NHC(O)–O–CH₂C₆H₅ | 10 | 8 | 4 | 9 | 0 3 | 7 | 9 | 7 | 2 | 0 | | | | 2 |
| | 4 | 8 | 2 | 8 | 0 2 | 0 | 5 | 0 | 0 | 0 | 0 | 0 | 0 | 0 |
| CH≡CCH₂O–C₆H₄–NHC(O)–O–C₆H₁₁ | 10 | 0 | 0 | 0 | 0 0 | 8 | 9 | 9 | 0 | 0 | | | | 0 |
| | 4 | 7 | 0 | 7 | 8 0 | 7 | 9 | 7 | 1 | 0 | 0 | 0 | 0 | 0 |
| CH≡CCH₂O–C₆H₄–NHC(O)–O–CH₂C≡CH | 10 | 8 | 9 | 9 | 3 2 | 2 | 5 | 6 | 0 | 0 | | | | 0 |
| | 4 | 7 | 0 | 0 | 0 0 | 0 | 0 | 0 | 0 | 0 | 0 | 1 | 0 | 1 |
| CH≡CCH₂O–C₆H₄–NHC(O)–O–CH(CH₃)C≡CH | 10 | 7 | 9 | 9 | 2 0 | 3 | 8 | 6 | 0 | 0 | | | | 0 |
| | 4 | 5 | 3 | 6 | 0 0 | 0 | 2 | 2 | 0 | 0 | 0 | 0 | 0 | 1 |
| CH₂=CHCH₂O–C₆H₃(Cl)–NHC(O)–O–CH₃ | 10 | 9 | 9 | 9 | 9 9 | 7 | 9 | 8 | 3 | 0 | | | | 7 |
| | 4 | 9 | 9 | 9 | 9 8 | 7 | 9 | 7 | 2 | 1 | 0 | 5 | 3 | 1 |
| | 1 | 9 | 9 | 9 | 5 2 | 6 | 5 | 2 | 1 | 1 | 0 | 2 | 2 | 0 |
| | 0.5 | 9 | 7 | 9 | 0 3 | 2 | 2 | 0 | 1 | 0 | 0 | 0 | 0 | 0 |
| | 0.25 | 8 | 7 | 7 | 0 0 | 0 | 0 | 0 | 0 | 0 | 0 | 0 | 0 | 0 |

We claim:
1. A method for the control of undesirable plant species comprising applying to said undesirable plants or locus of plants or seeds a herbicidally effective amount of a compound of the formula:

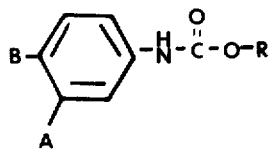

wherein A is hydrogen, chlorine or $-OCH_2C\equiv CH$; B is hydrogen, $-O-CH_2C\equiv CH$ or $-OCH_2CH=CH_2$ R is alkyl ($C_1-C_4$) benzyl, or cyclohexyl; provided that A and B are both not hydrogen.

2. A method according to claim 1 wherein the compound is of the formula:

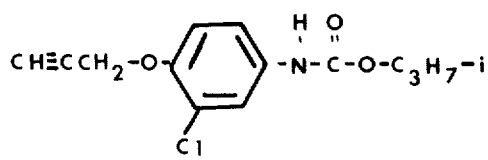

3. A method according to claim 1 wherein the compound is of the formula:

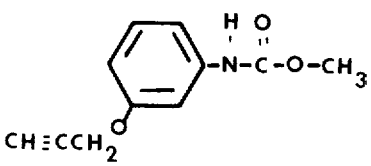

4. A method according to claim 1 wherein the compound is of the formula:

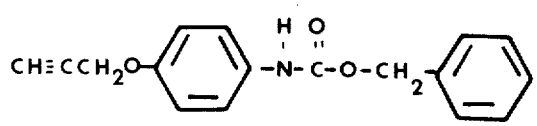

5. A method for the selective post-emergence control of undesirable plant species in the presence of agronomic crops, comprising applying to the foliage of said undesirable plants a herbicidally effective amount of a compound of the formula:

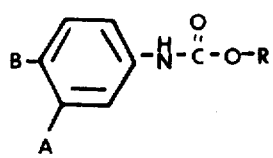

wherein A is hydrogen, chlorine or $-OCH_2C\equiv CH$; B is hydrogen, $-O-CH_2C\equiv CH$ or $-OCH_2CH=CH_2$ R is alkyl ($C_1-C_4$), benzyl, or cyclohexyl; provided that A and B are both not hydrogen.

6. A method for the selective preemergence control of undesirable plant species in the presence of agronomic crops, comprising applying to the soil containing seeds of said undesirable plants a herbicidally effective amount of a compound of the formula:

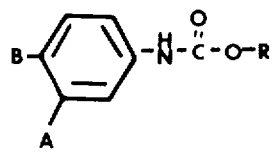

wherein A is hydrogen, chlorine or $-OCH_2C\equiv CH$; B is hydrogen, $-O-CH_2C\equiv CH$ or $-OCH_2CH=CH_2$ R is alkyl ($C_1-C_4$), benzyl, or cyclohexyl; provided that A and B are both not hydrogen.

7. A method according to claim 6 wherein the compound is:

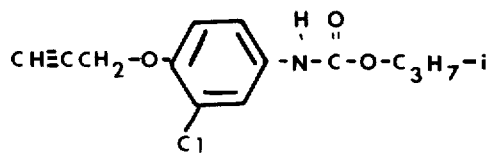

8. A method according to claim 6 wherein the compound is:

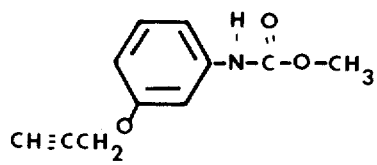

9. A method according to claim 6 wherein the compound is:

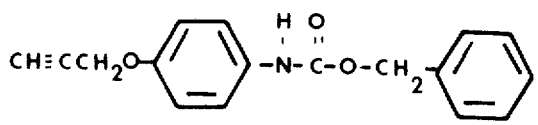

* * * * *